(12) United States Patent
Dreyfuss et al.

(10) Patent No.: US 10,052,091 B2
(45) Date of Patent: Aug. 21, 2018

(54) KNOTLESS SUTURE OR TISSUE FIXATION USING AN IMPLANT HAVING A POINTED TIP

(71) Applicant: Arthrex, Inc., Naples, FL (US)

(72) Inventors: Peter J. Dreyfuss, Naples, FL (US); Stephen S. Burkhart, Boerne, TX (US); Neil S. ElAttrache, Los Angeles, CA (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 13/765,218

(22) Filed: Feb. 12, 2013

(65) Prior Publication Data

US 2013/0150885 A1 Jun. 13, 2013

Related U.S. Application Data

(60) Division of application No. 13/182,893, filed on Jul. 14, 2011, now Pat. No. 8,430,909, which is a
(Continued)

(51) Int. Cl.
*A61B 17/04* (2006.01)
*A61F 2/08* (2006.01)
(Continued)

(52) U.S. Cl.
CPC ........ *A61B 17/0401* (2013.01); *A61F 2/0805* (2013.01); *A61F 2/0811* (2013.01);
(Continued)

(58) Field of Classification Search
CPC ... A61B 17/0401; A61F 2/0805; A61F 2/0811
(Continued)

(56) References Cited

U.S. PATENT DOCUMENTS

| 2,121,193 A | 6/1938 | Hanicke |
| 2,329,398 A | 9/1943 | Duffy |

(Continued)

FOREIGN PATENT DOCUMENTS

| CA | 2045903 C | 11/2001 |
| EP | 1016377 A2 | 4/2006 |

(Continued)

OTHER PUBLICATIONS

Arthrex, Inc., "PushLock SP," screenprints, pp. 1/8 to 8/8 and animation, Oct. 15, 2007. http://www.arthrex.com/resources/animation/sjjiLfkEEeCRTQBQVoRHOw/pushlock-sp.
(Continued)

*Primary Examiner* — Vy Bui
(74) *Attorney, Agent, or Firm* — Carlson, Gaskey & Olds

(57) ABSTRACT

A method for securing soft tissue to bone which does not require the surgeon to tie suture knots to secure the tissue to the bone. Suture is passed through the tissue at desired points. A cannulated plug or screw is pre-loaded onto the distal end of a driver provided with an eyelet implant at its distal end. Suture attached to the tissue is passed through the eyelet of the implant located at the distal end of the driver. The distal end of the driver together with the eyelet implant is inserted into the bone. Tension is applied to the suture to position the tissue at the desired location relative to the bone. The screw or plug is advanced into the pilot hole by turning the interference screw or tapping the plug until the cannulated screw or plug securely engages and locks in the eyelet implant, so that the cannulated plug or screw with the engaged eyelet implant is flush with the bone. Once the screw or plug is fully inserted and the suture is secured in the bone, the driver is removed and any loose ends of the sutures protruding from the anchor site are then clipped short.

20 Claims, 12 Drawing Sheets

Related U.S. Application Data continuation of application No. 12/022,868, filed on Jan. 30, 2008, now Pat. No. 7,993,369, which is a continuation-in-part of application No. 10/405,707, filed on Apr. 3, 2003, now Pat. No. 7,329,272, which is a continuation-in-part of application No. 09/886,280, filed on Jun. 22, 2001, now Pat. No. 6,544,281.

(60) Provisional application No. 60/213,263, filed on Jun. 22, 2000.

(51) Int. Cl.
  *A61B 17/86* (2006.01)
  *A61B 17/88* (2006.01)
  *A61B 17/00* (2006.01)

(52) U.S. Cl.
  CPC ......... *A61B 17/864* (2013.01); *A61B 17/8645* (2013.01); *A61B 17/8875* (2013.01); *A61B 2017/00907* (2013.01); *A61B 2017/0403* (2013.01); *A61B 2017/044* (2013.01); *A61B 2017/045* (2013.01); *A61B 2017/0409* (2013.01); *A61B 2017/0414* (2013.01); *A61B 2017/0445* (2013.01); *A61B 2017/0448* (2013.01); *A61F 2002/0835* (2013.01); *A61F 2002/0852* (2013.01); *A61F 2002/0858* (2013.01); *A61F 2002/0888* (2013.01)

(58) Field of Classification Search
  USPC ................... 606/73, 75, 104, 139, 144, 232
  See application file for complete search history.

(56) References Cited

U.S. PATENT DOCUMENTS

| | | |
|---|---|---|
| 2,381,050 A | 8/1945 | Hardinge |
| 2,472,103 A | 6/1949 | Giesen |
| 2,490,364 A | 12/1949 | Livingston |
| 2,562,419 A | 7/1951 | Ferris |
| 2,699,774 A | 1/1955 | Livingston |
| 3,143,916 A | 8/1964 | Rice |
| 3,716,058 A | 2/1973 | Tanner, Jr. |
| 3,768,635 A | 10/1973 | Eggert |
| 3,842,825 A | 10/1974 | Wagner |
| 3,910,281 A | 10/1975 | Kletschka et al. |
| 3,951,261 A | 4/1976 | Mandel |
| 3,990,438 A | 11/1976 | Pritchard |
| 4,006,747 A | 2/1977 | Kronenthal |
| 4,013,071 A | 3/1977 | Rosenberg et al. |
| 4,135,623 A | 1/1979 | Thyen |
| 4,244,370 A | 1/1981 | Furlow et al. |
| 4,275,717 A | 6/1981 | Bolesky et al. |
| 4,301,551 A | 11/1981 | Dore et al. |
| 4,351,069 A | 9/1982 | Ballintyn, Jr. et al. |
| 4,424,898 A | 1/1984 | Thyen et al. |
| 4,454,875 A | 6/1984 | Pratt et al. |
| 4,467,478 A | 8/1984 | Jurgutis et al. |
| 4,483,023 A | 11/1984 | Hoffman, Jr. et al. |
| 4,507,817 A | 4/1985 | Staffeld |
| 4,519,100 A | 5/1985 | Wills et al. |
| 4,520,511 A | 6/1985 | Gianezio et al. |
| 4,537,185 A | 8/1985 | Stednitz |
| 4,539,981 A | 9/1985 | Tunc |
| 4,590,928 A | 5/1986 | Hunt et al. |
| 4,597,776 A | 7/1986 | Ullman et al. |
| 4,605,414 A | 8/1986 | Czajka et al. |
| 4,632,100 A | 12/1986 | Somers et al. |
| 4,633,869 A | 1/1987 | Schmieding et al. |
| 4,640,271 A | 2/1987 | Lower et al. |
| 4,672,957 A | 6/1987 | Hourahane |
| 4,712,542 A | 12/1987 | Daniel et al. |
| 4,723,541 A | 2/1988 | Reese |
| 4,738,255 A | 4/1988 | Goble et al. |
| 4,741,330 A | 5/1988 | Hayhurst et al. |
| 4,750,492 A | 6/1988 | Jacobs et al. |
| 4,784,126 A | 11/1988 | Hourahane |
| 4,898,156 A | 2/1990 | Gatturna et al. |
| 4,946,467 A | 8/1990 | Ohi et al. |
| 4,946,468 A | 8/1990 | Li |
| 4,963,144 A | 10/1990 | Huene |
| 4,976,715 A | 12/1990 | Bays et al. |
| 5,002,550 A | 3/1991 | Li |
| 5,019,079 A | 5/1991 | Ross |
| 5,037,422 A | 8/1991 | Hayhurst et al. |
| 5,041,129 A | 8/1991 | Hayhurst et al. |
| 5,047,030 A | 9/1991 | Draenert |
| 5,100,417 A | 3/1992 | Cerier et al. |
| 5,100,471 A | 3/1992 | Winnik et al. |
| 5,102,421 A | 4/1992 | Anspach, Jr. |
| 5,141,520 A | 8/1992 | Goble |
| 5,152,790 A | 10/1992 | Rosenberg et al. |
| 5,156,616 A | 10/1992 | Meadows et al. |
| D331,463 S | 12/1992 | Rosenberg et al. |
| 5,176,682 A | 1/1993 | Chow et al. |
| 5,207,679 A | 5/1993 | Li |
| 5,217,486 A | 6/1993 | Rice et al. |
| 5,224,946 A | 7/1993 | Hayhurst et al. |
| 5,236,445 A | 8/1993 | Hayhurst et al. |
| 5,258,016 A | 11/1993 | Dipoto et al. |
| 5,261,914 A | 11/1993 | Warren |
| 5,268,001 A | 12/1993 | Nicholson et al. |
| 5,275,176 A | 1/1994 | Chandler et al. |
| 5,285,016 A | 2/1994 | Narizuka et al. |
| 5,312,438 A | 5/1994 | Johnson |
| 5,320,626 A | 6/1994 | Schmieding |
| 5,330,468 A | 7/1994 | Burkhart |
| 5,336,240 A | 8/1994 | Metzler et al. |
| 5,350,383 A | 9/1994 | Schmieding et al. |
| 5,364,400 A | 11/1994 | Rego, Jr. et al. |
| 5,370,662 A | 12/1994 | Stone et al. |
| 5,375,956 A | 12/1994 | Pennig |
| 5,380,334 A | 1/1995 | Torrie et al. |
| 5,383,905 A | 1/1995 | Golds |
| D357,534 S | 4/1995 | Hayes |
| 5,403,136 A | 4/1995 | Mathys et al. |
| 5,417,533 A | 5/1995 | Lasner |
| 5,417,691 A | 5/1995 | Hayhurst et al. |
| D359,557 S | 6/1995 | Hayes |
| 5,423,860 A | 6/1995 | Lizardi et al. |
| 5,441,502 A | 8/1995 | Bartlett et al. |
| 5,441,508 A | 8/1995 | Gazielly et al. |
| 5,443,482 A | 8/1995 | Stone et al. |
| 5,464,427 A | 11/1995 | Curtis et al. |
| 5,466,243 A | 11/1995 | Schmieding et al. |
| 5,501,695 A | 3/1996 | Anspach, Jr. et al. |
| 5,501,696 A | 3/1996 | Trott et al. |
| 5,520,692 A | 5/1996 | Ferrante et al. |
| 5,522,843 A | 6/1996 | Zang |
| 5,522,844 A | 6/1996 | Johnson |
| 5,527,342 A | 6/1996 | Pietrak et al. |
| 5,534,011 A | 7/1996 | Greene et al. |
| 5,545,180 A | 8/1996 | Le et al. |
| 5,562,664 A | 10/1996 | Durlacher et al. |
| 5,569,305 A | 10/1996 | Bonutti et al. |
| 5,569,306 A | 10/1996 | Thal |
| 5,573,547 A | 11/1996 | Leveen et al. |
| 5,573,548 A | 11/1996 | Nazre et al. |
| 5,575,801 A | 11/1996 | Habermeyer et al. |
| 5,575,819 A | 11/1996 | Amis et al. |
| 5,578,057 A | 11/1996 | Wenstrom |
| 5,584,835 A | 12/1996 | Greenfield et al. |
| 5,584,839 A | 12/1996 | Gieringer |
| 5,591,207 A | 1/1997 | Coleman |
| 5,593,425 A | 1/1997 | Bonutti et al. |
| 5,601,557 A | 2/1997 | Hayhurst et al. |
| 5,607,432 A | 3/1997 | Fucci |
| 5,624,446 A | 4/1997 | Harryman, II |
| 5,634,926 A | 6/1997 | Jobe et al. |
| 5,643,273 A | 7/1997 | Clark |
| 5,643,320 A | 7/1997 | Lower et al. |
| 5,643,321 A | 7/1997 | Mcdevitt |
| 5,645,545 A | 7/1997 | Bryant |
| 5,645,547 A | 7/1997 | Coleman et al. |

(56) References Cited

U.S. PATENT DOCUMENTS

| | | | |
|---|---|---|---|
| 5,645,589 A | 7/1997 | Li | |
| 5,647,874 A | 7/1997 | Hayhurst et al. | |
| 5,649,963 A | 7/1997 | McDevitt | |
| 5,658,313 A | 8/1997 | Thal | |
| 5,662,658 A | 9/1997 | Wenstrom, Jr. | |
| 5,665,112 A | 9/1997 | Thal | |
| 5,667,509 A | 9/1997 | Westin et al. | |
| D385,352 S | 10/1997 | Bales et al. | |
| 5,681,318 A | 10/1997 | Pennig et al. | |
| 5,681,333 A | 10/1997 | Burkhart et al. | |
| 5,683,401 A | 11/1997 | Schmieding et al. | |
| 5,683,419 A | 11/1997 | Thal | |
| 5,685,313 A | 11/1997 | Mayevsky | |
| 5,690,649 A | 11/1997 | Li et al. | |
| 5,690,676 A | 11/1997 | Dipoto et al. | |
| 5,690,677 A | 11/1997 | Schmieding et al. | |
| 5,697,950 A | 12/1997 | Fucci et al. | |
| 5,702,397 A | 12/1997 | Goble et al. | |
| 5,702,398 A | 12/1997 | Tarabishy et al. | |
| 5,707,394 A | 1/1998 | Miller et al. | |
| 5,709,708 A | 1/1998 | Thal et al. | |
| 5,720,765 A | 2/1998 | Thal | |
| 5,725,529 A | 3/1998 | Nicholson et al. | |
| 5,725,541 A * | 3/1998 | Anspach et al. | 606/151 |
| 5,728,136 A | 3/1998 | Thal | |
| 5,733,307 A | 3/1998 | Dinsdale | |
| 5,741,300 A | 4/1998 | Li | |
| 5,749,878 A | 5/1998 | Bracy et al. | |
| 5,755,721 A | 5/1998 | Hearn | |
| 5,782,864 A | 7/1998 | Lizardi | |
| 5,782,865 A | 7/1998 | Grotz | |
| 5,791,899 A | 8/1998 | Sachdeva et al. | |
| 5,797,963 A | 8/1998 | McDevitt | |
| 5,810,854 A | 9/1998 | Beach | |
| 5,814,071 A | 9/1998 | McDevitt et al. | |
| 5,824,011 A | 10/1998 | Stone et al. | |
| 5,827,291 A | 10/1998 | Fucci et al. | |
| 5,843,087 A | 12/1998 | Jensen et al. | |
| 5,843,127 A | 12/1998 | Li | |
| 5,860,978 A | 1/1999 | Mcdevitt et al. | |
| 5,860,983 A | 1/1999 | Wenstrom, Jr. | |
| 5,868,762 A | 2/1999 | Cragg et al. | |
| 5,868,789 A * | 2/1999 | Huebner | A61B 17/0401 606/232 |
| 5,879,372 A | 3/1999 | Bartlett et al. | |
| 5,891,168 A | 4/1999 | Thal et al. | |
| 5,893,850 A | 4/1999 | Cachia et al. | |
| 5,902,321 A | 5/1999 | Caspari et al. | |
| 5,935,129 A | 8/1999 | Mcdevitt et al. | |
| 5,948,000 A * | 9/1999 | Larsen | A61B 17/0469 606/232 |
| 5,948,001 A | 9/1999 | Larsen et al. | |
| 5,951,559 A | 9/1999 | Burkhart | |
| 5,957,953 A * | 9/1999 | DiPoto | A61B 17/0401 606/232 |
| 5,964,764 A | 10/1999 | West et al. | |
| 5,964,783 A | 10/1999 | Grafton et al. | |
| 5,968,044 A | 10/1999 | Nicholson et al. | |
| 5,980,558 A | 11/1999 | Wiley et al. | |
| 5,993,451 A | 11/1999 | Burkhart | |
| 6,007,567 A | 12/1999 | Bonutti | |
| 6,013,083 A | 1/2000 | Bennett | |
| 6,022,373 A | 2/2000 | Li | |
| 6,024,758 A | 2/2000 | Thal et al. | |
| 6,027,523 A | 2/2000 | Schmieding | |
| 6,030,162 A | 2/2000 | Huebner | |
| 6,036,694 A | 3/2000 | Goble et al. | |
| 6,045,573 A | 4/2000 | Wenstrom, Jr. et al. | |
| 6,045,574 A | 4/2000 | Thal et al. | |
| 6,056,751 A | 5/2000 | Fenton et al. | |
| 6,083,522 A | 7/2000 | Chu et al. | |
| 6,086,608 A | 7/2000 | Ek et al. | |
| 6,096,041 A | 8/2000 | Gellman et al. | |
| 6,117,162 A | 9/2000 | Schmieding et al. | |
| 6,129,762 A | 10/2000 | Li | |
| 6,143,017 A | 11/2000 | Thal | |
| 6,149,669 A | 11/2000 | Li | |
| 6,156,039 A | 12/2000 | Thal | |
| 6,159,235 A | 12/2000 | Kim | |
| 6,200,329 B1 | 3/2001 | Fung et al. | |
| 6,214,031 B1 | 4/2001 | Schmieding et al. | |
| 6,221,107 B1 | 4/2001 | Steiner et al. | |
| 6,231,592 B1 | 5/2001 | Bonutti et al. | |
| 6,280,474 B1 | 8/2001 | Cassidy et al. | |
| 6,287,324 B1 | 9/2001 | Yarnitsky et al. | |
| 6,319,270 B1 | 11/2001 | Grafton et al. | |
| 6,355,053 B1 | 3/2002 | Li | |
| RE37,963 E | 1/2003 | Thal | |
| 6,517,542 B1 | 2/2003 | Papay et al. | |
| 6,517,564 B1 | 2/2003 | Grafton et al. | |
| 6,520,980 B1 | 2/2003 | Foerster | |
| 6,524,317 B1 | 2/2003 | Ritchart et al. | |
| 6,527,794 B1 | 3/2003 | McDevitt et al. | |
| 6,527,795 B1 | 3/2003 | Lizardi | |
| 6,544,281 B2 | 4/2003 | ElAttrache et al. | |
| 6,551,330 B1 | 4/2003 | Bain et al. | |
| 6,558,389 B2 | 5/2003 | Clark et al. | |
| 6,562,044 B1 | 5/2003 | Cooper | |
| 6,585,730 B1 | 7/2003 | Foerster | |
| 6,592,609 B1 | 7/2003 | Bonutti | |
| 6,635,074 B2 | 10/2003 | Bartlett | |
| 6,641,596 B1 | 11/2003 | Lizardi et al. | |
| 6,641,597 B2 | 11/2003 | Burkhart et al. | |
| 6,652,561 B1 | 11/2003 | Tran | |
| 6,656,183 B2 | 12/2003 | Colleran et al. | |
| 6,660,008 B1 | 12/2003 | Foerster et al. | |
| 6,692,516 B2 * | 2/2004 | West, Jr. | A61B 17/0401 606/232 |
| 6,770,076 B2 | 8/2004 | Foerster | |
| 6,770,084 B2 | 8/2004 | Bain et al. | |
| 6,780,198 B1 | 8/2004 | Gregoire et al. | |
| 6,818,010 B2 | 11/2004 | Eichhorn et al. | |
| 6,840,953 B2 | 1/2005 | Martinek | |
| 6,857,520 B2 | 2/2005 | Salazar et al. | |
| 7,037,324 B2 | 5/2006 | Martinek | |
| 7,083,638 B2 | 8/2006 | Foerster | |
| 7,204,839 B2 | 4/2007 | Dreyfuss et al. | |
| 7,211,088 B2 | 5/2007 | Grafton et al. | |
| 7,247,164 B1 | 7/2007 | Ritchart et al. | |
| 7,329,272 B2 | 2/2008 | Burkhart et al. | |
| 7,491,217 B1 | 2/2009 | Hendren et al. | |
| 7,517,357 B2 | 4/2009 | Abrams et al. | |
| 7,556,640 B2 | 7/2009 | Foerster | |
| 7,637,949 B2 | 12/2009 | Hart | |
| 7,651,495 B2 | 1/2010 | McDevitt et al. | |
| 7,695,494 B2 | 4/2010 | Foerster | |
| 7,695,495 B2 | 4/2010 | Dreyfuss | |
| 7,785,347 B2 | 8/2010 | Harvie et al. | |
| 7,803,173 B2 | 9/2010 | Burkhart et al. | |
| 7,828,820 B2 * | 11/2010 | Stone et al. | 606/232 |
| 7,867,251 B2 * | 1/2011 | Colleran et al. | 606/232 |
| 7,887,551 B2 | 2/2011 | Bojarski et al. | |
| 7,981,140 B2 | 7/2011 | Burkhart | |
| 7,993,369 B2 | 8/2011 | Dreyfuss | |
| 8,105,343 B2 | 1/2012 | White et al. | |
| 8,133,258 B2 | 3/2012 | Foerster et al. | |
| 8,137,381 B2 | 3/2012 | Foerster et al. | |
| 8,317,829 B2 | 11/2012 | Foerster et al. | |
| 8,430,909 B2 | 4/2013 | Dreyfuss | |
| 8,444,672 B2 | 5/2013 | Foerster | |
| 8,696,703 B2 * | 4/2014 | Anspach et al. | 606/232 |
| 8,764,797 B2 | 7/2014 | Dreyfuss et al. | |
| 2002/0013608 A1 | 1/2002 | ElAttrache et al. | |
| 2002/0111653 A1 | 8/2002 | Foerster | |
| 2002/0128684 A1 | 9/2002 | Foerster | |
| 2002/0188305 A1 | 12/2002 | Foerster et al. | |
| 2003/0004545 A1 | 1/2003 | Burkhart et al. | |
| 2003/0065361 A1 | 4/2003 | Dreyfuss | |
| 2003/0069604 A1 | 4/2003 | Schmieding et al. | |
| 2003/0144696 A1 | 7/2003 | Sinnott et al. | |
| 2003/0149448 A1 | 8/2003 | Foerster et al. | |
| 2003/0191498 A1 | 10/2003 | Foerster et al. | |
| 2003/0195563 A1 | 10/2003 | Foerster | |
| 2004/0093031 A1 | 5/2004 | Burkhart et al. | |

(56) References Cited

U.S. PATENT DOCUMENTS

| | | |
|---|---|---|
| 2004/0138683 A1 | 7/2004 | Shelton |
| 2004/0267316 A1 | 12/2004 | Powell et al. |
| 2005/0222618 A1 | 10/2005 | Dreyfuss et al. |
| 2005/0245932 A1 | 11/2005 | Fanton et al. |
| 2005/0277986 A1 | 12/2005 | Foerster et al. |
| 2005/0283156 A1 | 12/2005 | Schmieding et al. |
| 2006/0004364 A1 | 1/2006 | Green et al. |
| 2006/0074434 A1 | 4/2006 | Wenstrom et al. |
| 2006/0079904 A1 | 4/2006 | Thal |
| 2006/0100630 A1 | 5/2006 | West, Jr. |
| 2007/0142838 A1 | 6/2007 | Jordan |
| 2007/0156148 A1 | 7/2007 | Fanton et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0191849 A1 | 8/2007 | ElAttrache et al. |
| 2007/0225719 A1 | 9/2007 | Stone et al. |
| 2007/0255317 A1 | 11/2007 | Fanton et al. |
| 2007/0260259 A1 | 11/2007 | Fanton et al. |
| 2008/0004659 A1 | 1/2008 | Burkhart et al. |
| 2009/0187216 A1 | 7/2009 | Schmieding et al. |
| 2011/0015674 A1 | 1/2011 | Howard et al. |
| 2013/0150885 A1 | 6/2013 | Dreyfuss |

FOREIGN PATENT DOCUMENTS

| | | |
|---|---|---|
| EP | 1797826 B1 | 12/2009 |
| FR | 2622430 A1 | 5/1989 |
| SU | 1600713 A1 | 10/1990 |
| WO | 9522930 | 8/1995 |
| WO | 99/37217 | 7/1999 |

OTHER PUBLICATIONS

CanMed Orthopedi, "Artroskopi Katagorisindeki Videolar" http://www.canmedortopedi.com.tr/videolar.html.

Meeks & Zilberfarb Orthopedis., "Patient Education" 2007. http://www.mzortho.com/pted-videos.htm.

Wikipedia, "Wikipedia Osseointegration" http://en.wikipedia.org/wiki/Osseointegration.

"The Autocuff™ System," Opus Medical, 2003.

Peter J. Millett, et al., "Mattress Double Anchor Footprint Repair: a Novel, Arthroscopic Rotator Cuff Repair Technique," Arthroscopy: The Journal of Arthroscopic and Related Surgery, vol. 20, No. 8 Oct. 2004: pp. 875-879.

Maria Apreleva, et al., "Rotator Cuff Tears: the Effect of the Reconstruction Method on Three-Dimensional Repair Site Area," Arthroscopy: The Journal of Arthroscopic and Related Surgery, vol. 18, No. 5 May-Jun. 2002: pp. 519-526.

Michael S. George, et al., "Suture Anchors in Arthroscopic Rotator Cuff Repair," Operative Techniques in Sports Medicine 12:210-214 @ 2004 Elsevier Inc.

Philip Bacilla, et al., "Arthroscopic Bankart Repair in a High Demand Patient Population," Arthroscope: The Journal of Arthroscopic and Related Surgery, vol. 13, No. 1 Feb. 1997, pp. 51-60.

Laurence D. Higgins, et al., "Athroscopic Bankart Repair, Operative Technique and Surgical Pitfalls," Management of the Unstable Shoulder: Arthroscopic Approaches for the Next Millennium, Clinics in Sports Medicine, vol. 19, No. 1, Jan. 2000.

Brian J. Cole, et al., "Arthroscopic Shoulder Stabilization With Suture Anchors; Technique, Technology, and Pitfalls," Clinical Orthopaedics and Related Research, vol. 390, Sep. 2001, pp. 17-30.

F. Alan Barber, et al., "Internal Fixation Strength of Suture Anchors—Updated 1997," Arthroscopy: The Journal of Arthroscopic and Related Surgery, vol. 13, No. 3 Jun. 1997: pp. 355-362.

Rudy Robbe, et al., "Knotless Suture-Based Anchors," Operative Techniques in Sports Medicine, 12:221-224 @ 2004 Elsevier Inc.

Raymond Thal, "Knotless Suture Anchor—Arthroscopic Bankart Repair Without Tying Knots," Clinical Orthopaedics and Related Research, No. 390, pp. 42-51 @2001 Lippincott Willliams & Wilkins, Inc.

Robert L. Waltrip, et al., "Rotator Cuff Repair; A Biomechanical Comparison of Three Techniques," The American Journal of Sports Medicine, pp. 493-497, http://ajs.sagepub.com.

Edward Yian, et al., "Arthroscopic Repair of Slap Lesions With a Bioknotless Suture Anchor," Arthroscopy: The Journal of Arthroscopic and Related Surgery, vol. 20, No. 5 May-Jun. 2004: pp. 547-551.

Matthias Zumstein, et al., "In vitro Comparison of Standard and Knotless Metal Suture Anchors," Arthroscopy: The Journal of Arthroscopic and Related Surgery, vol. 20, No. 5 May-Jun. 2004: pp. 517-520.

Arthroscopic Bankart Repair Using Suture Anchors, By: Eugene M. Wolf, MD, et al., Operative Techniques in Orthopaedics, vol. 1, No. 2 (Apr.), 191; pp. 184-191.

Repairs of the Rotator Cuff, Correlation of Functional Results with Integrity of the Cuff, By: Douglas T. Harryman II, M.D., et al., from the Shoulder and Elbow Service, Department of Orthopaedics, University of Washington, Seattle; Copyright 1991 by The Journal of Bone and Joint Surgery, Incorporated, pp. 982-989.

Modification of the Bankart Reconstruction With a Suture Anchor, By: John C. Richmond, M.D., et al., The American Journal of Sports Medicine, vol. 19, No. 4, 1991 American Orthopaedic Society for Sports Medicine, pp. 343-346.

Slap Lesions in Association With Complete Tears of the Long Head of the Biceps Tendon: a Report of Two Cases, By: Stephen S. Burkhart, M.D., and David L. Fox, M.D., Arthroscopy: The Journal of Arthroscopic and Related Surgery 8(1):31-35, Published by Raven Press, Ltd. @1992 Arthroscopy Association of North America.

Pull-Out Strength of Suture Anchors for Rotator Cuff and Bankart Lesion Repairs, By: Aaron T. Hecker, MS, et al., The American Journal of Sports Medicine, vol. 21, No. 6, @1993 American Orthopaedic Society for Sports Medicine, pp. 874-879.

Arthroscopic Capsulolabral Repair Using Suture Anchors, By: Eugene M. Wolf, MD; from the Department of Orthopaedic Surgery, California Pacific Medical Center, San Francisco, California, vol. 24, No. 1, Jan. 1993; pp. 59-69.

Mechanical Strength of Repairs of the Rotator Cuff, By: Christian Gerber, et al., From the Hopital Cantonal, Fribourg, the University of Berne and the AO Research Institute, Davos, Switzerland, The Journal of Bone and Joint Surgery, vol. 76-B, No. 3, May 1994; pp. 371-380.

Partial Repair of Irreparable Rotator Cuff Tears, By: Stephen S. Burkhart, M.D., et al., Arthroscopy: The Journal of Arthroscopic and Related Surgery, Arthroscopy, vol. 10, No. 4, 1994, pp. 363-370.

The in vivo Histology of an Absorbable Suture Anchor: a Preliminary Report, By; A. Alan Barber, M.D. and Michael A. Deck, M.D., Arthroscopy: The Journal of Arthroscopic and Related Surgery, vol. 11, No. 1 Feb. 1995; pp. 77-81.

The Deadman Theory of Suture Anchors: Observations Along a South Texas Fence Line, By: Stephen S. Burkhart, M.D., Arthroscopy: The Journal of Arthroscopic and Related Surgery, vol. 11, No. 1 Feb. 1995; pp. 119-123.

The Ultimate Strength of Suture Anchors, By: F. Alan Barber, M.D., et al., Arthroscopy: The Journal of Arthroscopic and Related Surgery, vol. 11, No. 1 Feb. 1995; pp. 21-28.

Full-Thickness Rotator Cuff Tears, A Biomechanical Comparison of Suture Versus Bone Anchor Techniques, By: Stephen C. Reed, et al., The American Journal of Sports Medicine, vol. 24, No. 1, pp. 46-48.

Fixation Strength of Rotator Cuff Repairs With Suture Anchors and the Transosseous Suture Technique, By: David V. Craft, MD, et al., 1996 by Journal of Shoulder and Elbow Surgery Board of Trustees, pp. 32-40.

Suture Anchor Strength Revisited, By: F. Alan Barber, M.D., et al., Arthroscopy: The Journal of Arthroscopic and Related Surgery, vol. 12, No. 1 Feb. 1996; pp. 32-38.

Technique of Arthroscopic Rotator Cuff Repair Using Implantable 4-MM Revo Suture Anchors, Suture Shuttle Relays, and No. 2

(56) References Cited

OTHER PUBLICATIONS

Nonabsorbable Mattress Sutures, By: Stephen J. Snyder, MD, The Rotator Cuff, Part II, vol. 28, No. 2, Apr. 1997, pp. 267-275.
Internal Fixation Strength of Suture Anchors—Update 1997, By: F. Alan Barber, M.D., et al., Arthroscopy: The Journal of Arthroscopic and Related Surgery, vol. 13, No. 3, Jun. 1997; pp. 355-362.
Cyclic Loading of Anchor-Based Rotator Cuff Repairs: Confirmation of the Tension Overload Phenomenon and Comparison of Suture Anchor Fixation With Transosseous Fixation, By: Stephen S. Burkhart, M.D., et al., Arthroscopy: The Journal of Arthroscopic and Related Surgery, vol. 13, No. 6 Dec. 1997; pp. 720-724.
Suture Anchors—Update 1999, By: F. Alan Barber, M.D. and Morley A. Herbert PhD., Arthroscopy: The Journal of Arthroscopic and Related Surgery, vol. 15, No. 7 Oct. 1999; pp. 719-725.
Evaluation of a High Density Polyethylene Fixing System for Hydroxyapatite Ceramic Implants, By: Ichiro Ono, et al., Biomaterials 21 (2000) 143-151.
Knotless Suture Anchor, Arthroscopic Bankard Repair Without Tying Knots, by: Raymond Thal, MD, Clinical Orthopaedics and Related Research, No. 390, pp. 42-51.
Bioknotless Anchor, Mitek Products.
Fatigue Testing of Suture Anchors, By: Stefan Rupp, MD, et al., The American Journal of Sports Medicine, vol. 30, No. 2, 2002, pp. 239-247.
Failure of Suture Material at Suture Anchor Eyelets, By: Dominik C. Meyer, M.D., et al., Arthroscopy: The Journal of Arthroscopic and Related Surgery, vol. 18, No. 9 Nov.-Dec. 2002; pp. 1013-1019.
Arthroscopic Management of Partial, Full-Thickness, and Complex Rotator Cuff Tears: Indications, Techniques, and Complications, By: Eric S. Millstein, M.D., Arthroscopy: The Journal of Arthroscopic and Related Surgery, vol. 19, No. 10 (Dec., Suppl 1), 2003: pp. 189-199.
Suture Anchor Failure Strength—an in vivo Study, By: F. Alan Barber, M.D., et al., Arthroscopy, vol. 9, No. 6, 1993.
Sutures and Suture Anchors: Update 2003, By: F. Alan Barber, M.D, et al., Arthroscopy: The Journal of Arthroscopic and Related Surgery, vol. 19, No. 9 Nov. 2003: pp. 985-990.
Sutures and Suture Anchors—Update 2006, By: F. Alan Barber, M.D., et al., Arthroscopy: The Journal of Arthroscopic and Related Surgery, vol. 22, No. 10 Oct. 2006; pp. 1063-1069.
Arthrex Is Reaching New Heights in Rotator Cuff Repair, eight pages, Copyright Arthrex, Inc., 2007.
Biodegradable Shoulder Anchors Have Unique Modes of Failure, By: F. Alan Barber, M.D., Arthroscopy: The Journal of Arthroscopic and Related Surgery, vol. 23, No. 3 Mar. 2007; pp. 316-320.
Practical Orthopaedic Sports Medicine and Arthroscopy, By: Donald H. Johnson, MD, FRCS, et al., 2007 by Lippincott Williams & Wilkins, a Wolters Klewer business, Chapter 20: Thermal Treatment, Sutures, Knots and Bone Anchors, pp. 303-305.
Arthroscopic Rotator Cuff Surgery, A Practical Approach to Management, By: Jeffrey S. Abrams and Robert H. Bell, ISBN: 978-0-387-39340-7.
Suture Anchor Materials, Eyelets, and Designs: Update 2008, By: F. Alan Barber, MD, et al., Arthroscopy: The Journal of Arthroscopic and Related Surgery, vol. 24, No. 8 Aug. 2008: pp. 859-867.
Biomechanical Stability of Knotless Suture Anchors Used in Rotator Cuff Repair in Healthy and Osteopenic Bone, By: Matthias F. Pietschmann, M.D, et al., Arthroscopy: The Journal of Arthroscopic and Related Surgery, vol. 26, No. 8 Aug. 2010: pp. 1035-1044.
Biomechanical Analysis of Pullout Strengths of Rotator Cuff and Glenoid Anchors: 2011 Update, By: F. Alan Barber, M.D., et al., Arthroscopy: The Journal of Arthroscopic and Related Surgery, vol. 27, No. 7 Jul. 2011: pp. 895-905.
Arthroscopic Rotator Cuff Repair: Suture Anchor Properties, Modes of Failure and Technical Considerations, By: Richard Ma, et al., Expert Rev. Med. Devices 8(3), 377-387 (2011).
Applications of Polyetheretherketone in Trauma, Arthroscopy, and Cranial Defect Repair, By: Scott Lovald Ph.D., and Steven M. Kurtz, Ph.D., Chapter 15, PEEK Biomaterials Handbook. DOI: 10.1016/B978-1-4377-4463.7.10015-6, Copyright 2012 Elsevier Inc, pp. 243-259.
The Evolution of Suture Andchors in Arthroscopic Rotator Cuff Repair, By: Patrick J. Denard, M.D. and Stephen S. Burkhart, M.D., Arthroscopy: The Journal of Arthroscopic and Related Surgery, vol. 29, No. 9 Sep. 2013; pp. 1589-1595.
The Autocuff System, Opus Medical, four pages, Copyright 2003, www.opusmedical.com.
Current Concept of Rotator Cuff Repair, By: Stephen S. Burkhart and Wesley M. Nottage, Chapter 4, pp. 81-88.
501(k) Summary of Safety and Effectiveness, By: Carol A. Weideman, Ph.D., six pages, Linvatek, Mar. 21, 1997.
501(k) Summary of Safety and Effectiveness, one page, DePuy, Inc., Feb. 6, 1997.
United States Patent and Trademark Office, Before the Patent Trial and Appeal Board, *Smith & Nephew, Inc. & Arthrocare Corporation v Arthrex, Inc.*, Case IPR2017-00275, U.S. Pat. No. 9,179,907; Patent Owner Arthrex, Inc.'s Preliminary Response Pursuant to 37 C.F.R. 42.107.
Hecker, et al.; Pull-out strength of suture anchors for rotator cuff and Bankart lesion repairs; The American Journal of Sports Medicine, vol. 21, No. 6, 1993 American Orthopaedic Society for Sports Medicine; pp. 874-879 (S&N Exhibit 1022; *S&N v. Arthrex*).
United States Patent and Trademark Office, Before the Patent Trial and Appeal Board, *Smith & Nephew, Inc. & Arthrocare Corporation v Arthrex, Inc.*, Case No. IPR201700275, U.S. Pat. No. 9,179,907; Declaration of Dr. David R. McAllister dated Nov. 13, 2016, 127 pages (S&N Exhibit 1019; *S&N v Arthrex*).
Correspondence to Mr. Mark Ritchart, President and CEO, Opus Medical, Inc., from Celia Witten, M.D., Director, Division of General, Restorative and Neurological Devices, Department of Health & Human Services, dated Sep. 17, 2001; 3 pages (S&N Exhibit 1016; *S&N v Arthrex*).
Mitek Products, 510(k) Summary for K974345 dated Feb. 13, 1998, 5 pages (S&N Exhibit 1015; *S&N v Arthrex*).
United States Patent and Trademark Office, Before the Patent Trial and Appeal Board, *Smith & Nephew, Inc. & Arthrocare Corporation v Arthrex, Inc.*, Case No. IPR201700275, U.S. Pat. No. 9,179,907; Petition for Inter Partes Review Under 35 U.S.C. §§ 311-19 and 37 C.F.R. § 42.1 et seq., dated Nov. 15, 2016, 75 pages.
Barber, et al.; Suture Anchors-Update 1999; Arthroscopy: The Journal of Arthroscopic and Related Surgery, vol. 15, No. 7 Oct. 1999; pp. 719-725 (S&N Exhibit 1025; *S&N v Arthrex*).
Barber, et al.; Suture Anchor Strength Revisited; Arthroscopy: The Journal of Arthroscopic and Related Surgery, vol. 12, No. 1 Feb. 1996; pp. 32-38 (S&N Exhibit 1024; *S&N v Arthrex*).
Barber, et al.; Suture Anchor Failure Strength—An In Vivo Study; Arthroscopy: The Journal of Arthroscopic and Related Surgery, 9(6):647-652; Published by Raven Press, Ltd., 1993 Arthroscopy Association of North America (S&N Exhibit 1023; *S&N v Arthrex*).
*Smith & Nephew, Inc. et al. v Arthrex, Inc.*, Case IPR2017-00275, U.S. Pat. No. 9,179,907, Patent Owner Arthrex, Inc.'s Response Pursuant to 37 C.F.R. §42.120 dated Aug. 18, 2017.
Disclaimer in Patent Under 37 CFR 1.321(a), U.S. Pat. No. 9,179,907, dated Feb. 28, 2017 (Arthrex Exhibit 2001, *Smith & Nephew v. Arthrex*, Case IPR2017-00275).
Declaration of Dr. Geoffrey B. Higgs dated Aug. 18, 2017 (Arthrex Exhibit 2037, *Smith & Nephew v. Arthrex*, Case IPR2017-00275).
Excerpt of 1999 Oxford Dictionary (Arthrex Exhibit 2009, *Smith & Nephew v. Arthrex*, Case IPR2017-00275).
Arthrex Bio-Corkscrew Suture Anchor Brochure (2000) (Arthrex Exhibit 2014, *Smith & Nephew v. Arthrex*, Case IPR2017-00275).
Arthrex Corkscrew Rotator Cuff Repair Technique Guide (1998) (Arthrex Exhibit 2017, *Smith & Nephew v. Arthrex*, Case IPR2017-00275).
Transcript of Jul. 21, 2017, Deposition of Dr. David McAllister (Arthrex Exhibit 2022, *Smith & Nephew v. Arthrex*, Case IPR2017-00275).
US Patent and Trademark Office, Before the Patent Trial and Appeal Board, Case No. IPR2017-00275, U.S. Pat. No. 9,179,907B2, *Smith*

*(56)* References Cited

OTHER PUBLICATIONS

& *Nephew, Inc., et al.* v *Arthrex, Inc.*, Paper 7, Entered May 10, 2017, "Decision Granting Institution of Inter Partes Review, 37 C.F.R. § 42.108".

* cited by examiner

KNOTLESS SUTURE OR TISSUE FIXATION USING AN IMPLANT HAVING A POINTED TIP

This is a divisional of U.S. application Ser. No. 13/182,893, filed Jul. 14, 2011, now U.S. Pat. No. 8,430,909, which is a continuation of U.S. application Ser. No. 12/022,868, filed Jan. 30, 2008, now U.S. Pat. No. 7,993,369, which is a continuation-in-part of U.S. application Ser. No. 10/405,707, filed Apr. 3, 2003, now U.S. Pat. No. 7,329,272, which is a continuation-in-part of U.S. application Ser. No. 09/886,280, filed Jun. 22, 2001, now U.S. Pat. No. 6,544,281, which claims the benefit of U.S. Provisional Application No. 60/213,263, filed Jun. 22, 2000.

FIELD OF THE INVENTION

The present invention relates to methods and instruments for fixation of sutures and tissue to bone.

BACKGROUND OF THE INVENTION

When soft tissue such as a ligament or a tendon becomes detached from a bone, surgery is usually required to reattach or reconstruct the tissue. Often, a tissue graft is attached to the bone to facilitate regrowth and permanent attachment. Various fixation devices, including sutures, screws, staples, wedges, and plugs have been used in the past to secure soft tissue to bone. For example, in typical interference screw fixation, the graft is fixed to the bone by driving the screw into a blind hole or a tunnel in the bone while trapping the end of the graft between the screw and the bone tunnel. In other methods, the graft is simply pinned against the bone using staples or sutures tied around the end of the graft to the bone.

Application Ser. No. 09/886,280 filed on Jun. 22, 2001, the disclosure of which is incorporated by reference herein, discloses a surgical technique and associated instruments for securing soft tissue to bone which does not require the surgeon to tie suture knots to secure the tissue to the bone. According to the technique, a cannulated plug or screw is pre-loaded onto the distal end of a cannulated driver, and a suture or wire loop is passed through the cannula of the driver so that a looped end of the suture or wire is exposed at the distal end of the driver. Suture strands attached to a graft are fed through the loop at the end of the driver, and the driver is inserted into the bottom of the hole, with the screw or plug disposed just outside the hole. With tension applied to the suture or wire loop to keep the graft at the desired location relative to the bone hole, the screw or plug is then fully advanced into the hole using the driver to frictionally secure either the suture attached to the graft or the graft itself into the bone hole.

Although the above-described technique provides an improved method of graft fixation to bone, the flexible loop configuration at the end of the driver disadvantageously impedes sliding of the suture or graft which is fed through the suture loop. In addition, because the cannulated driver of application Ser. No. 09/886,280 is provided with a flexible loop at its distal end, placement of the suture or graft at the bottom of the blind hole or socket and the cortical bone must be approximated, thus sometimes necessitating additional removal, tapping and insertion steps to ensure full insertion of the plug or screw into the blind hole or socket. This, in turn, may abrade the adjacent tissue and/or damage the bone or cartilage.

Accordingly, a need exists for an improved surgical technique and associated device for securing soft tissue to bone which allows the free sliding of the suture ends attached to a graft to ensure the positioning of the graft at an appropriate distance from the device. A fixation device and associated surgical technique that allow precise advancement and guiding of the plug or screw into the blind hole or socket are also needed.

SUMMARY OF THE INVENTION

The instruments and methods of the present invention overcome the disadvantages of the prior art, such as those noted above, by providing an eyelet implant at the distal end of a driver that securely engages and locks into a cannulated ribbed body of an interference plug or screw. The eyelet implant includes a fixed aperture for receiving a suture attached to a graft, such that the suture is able to freely slide through the aperture.

In one embodiment of the invention, suture is passed through the graft at desired points. A cannulated plug or screw is pre-loaded onto a driver provided with an eyelet implant at its distal end. Suture attached to the graft is passed through an aperture of the eyelet implant located at the distal end of the driver. The distal end of the driver together with the eyelet implant is inserted directly into the bone. The screw or plug is fully advanced into the pilot hole by tapping the interference screw or plug until the cannulated plug or screw securely engages and locks in the eyelet implant. Once the screw or plug is fully inserted and the suture is impacted into the bone, the driver is removed.

Other features and advantages of the invention will become apparent from the following description of the invention, which refers to the accompanying drawings.

DETAILED DESCRIPTION OF THE PREFERRED EMBODIMENT

Figure 1:
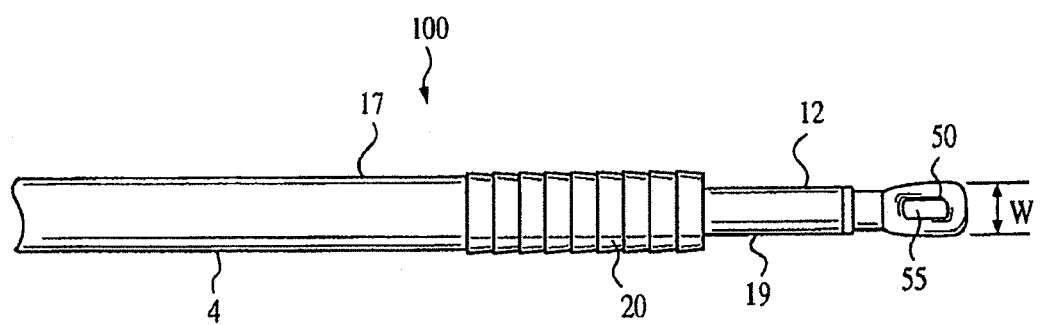
FIG. 1 illustrates a perspective view of a distal end of a push lock driver of the present invention.
Figure 2:
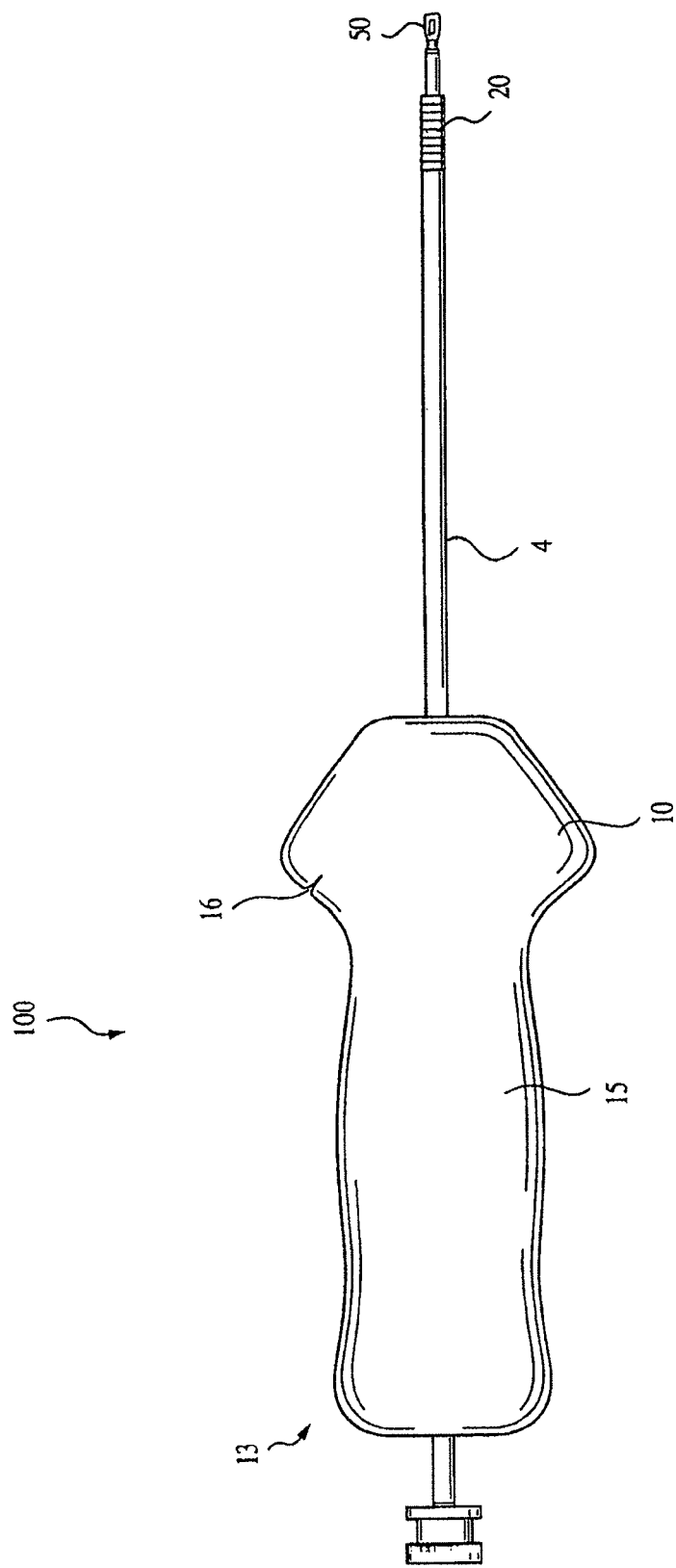
FIG. 2 illustrates a perspective view of a push lock driver of the present invention.

Referring now to the drawings, where like elements are designated by like reference numerals, FIGS. 1 and 2 illustrate an implant driver 100 of the present invention. Driver 100 includes a body 4, preferably in the form of a cylinder, and having a distal end 12 (FIG. 1) and a proximal end 13 (FIG. 2). The body 4 of driver 100 includes an outer shaft 17 and an inner shaft 19. The outer shaft 17 is cannulated for receiving inner shaft 19.

As illustrated in FIG. 1, driver 100 is pre-loaded with an interference device 20. Preferably, the interference device 20 is a screw or an interference plug, preferably formed of a bioabsorbable material such as PLLA. If a screw is employed, the screw may be provided with a cannulated body provided with a continuous thread having rounded outer edges. The head of the screw may be rounded to minimize abrasion or cutting of tissue. The cannulation formed through the screw is preferably hex-shaped and accepts the correspondingly shaped inner shaft 19 of driver 100. If an interference plug is desired, the plug is provided with rounded annular ribs separated by rounded annular grooves. The outer diameter of the ribs and grooves is substantially constant. The plug tapers significantly toward the distal end. The plug also comprises a cannula, preferably hex-shaped, for accommodating the inner correspondingly shaped shaft 19 of the corresponding driver 100.

As also shown in FIG. 1, an eyelet implant 50 is provided at the distal end 12 of driver 100. The eyelet implant 50 is releasably attached to the distal end 12 of driver 100 by means of a connector 57. The eyelet implant 50 is formed of a transparent polymer material, and is preferably made of a bioabsorbable material such as PLLA, polyglycolic or polylactic acid polymers. Advantageously, the eyelet implant 50 is made of a material similar to that of the interference device 20. As illustrated in FIG. 1, the eyelet implant 50 is provided with aperture 55 for receiving a suture attached to a graft to pass through the eyelet implant 50, as described in more detail below. The width "w" (FIG. 1) of the eyelet implant 50 is about equal the diameter of the inner shaft 19 and slightly smaller than the diameter of the outer shaft 17 and of the cannula of the interference device 20.

FIG. 2 illustrates proximal end 13 of driver 100, showing a handle 15 disposed coaxially with the body 4 and outer shaft 17 and provided with handle slots or protuberances 16. As described below, handle slots or protuberances 16 allow a suture strand to be wrapped around the handle 15 and be subsequently tensioned prior to the impaction of the interference device 20 into the pilot hole. In this manner, the graft is precisely positioned at an appropriate distance from the pilot hole, and the suture with the attached graft is secured at the bottom of the pilot hole and prevented from exiting the pilot hole.

Figure 3:
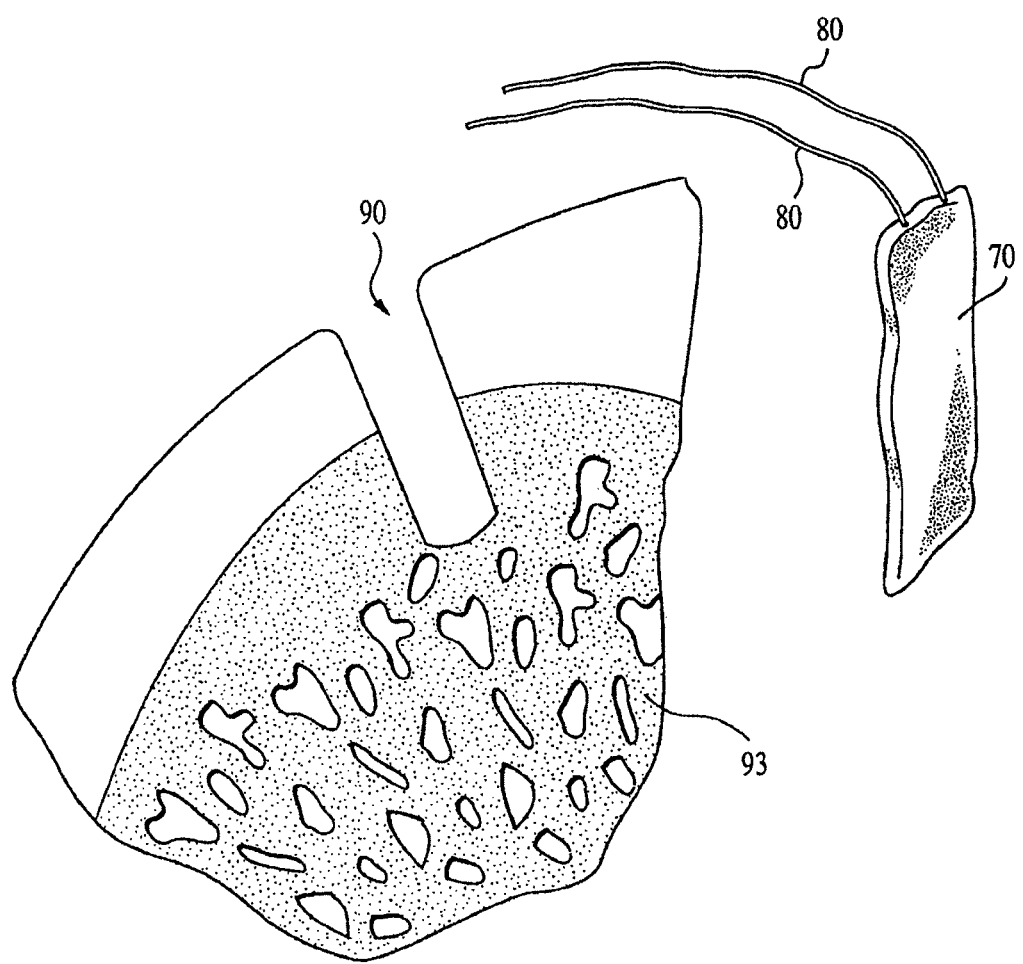
FIG. 3 is a schematic cross-sectional view of a surgical site undergoing a graft fixation technique according to a method of the present invention.

A method of a graft fixation technique according to the present invention is now described with reference to FIGS. 3-8. The present invention may be used to secure any type of soft tissue, graft, or tendon, such as, for example, a biceps tendon or a rotator cuff. FIG. 3 illustrates at least one suture 80 passed though the graft 70 at desired points. FIG. 3 also illustrates a pilot hole or socket 90 formed in the bone or cartilage 93 using a drill or punch, at the location where the tissue is to be secured. A punch provides the advantages of rounding the opening edge of the bone socket to protect the sutures 80 attached to the graft 70 from being sheared during the insertion process, and also compacts the bone at the punch site for better attachment of the bone by the anchor in cases where the bone is a soft bone.

Figure 4:
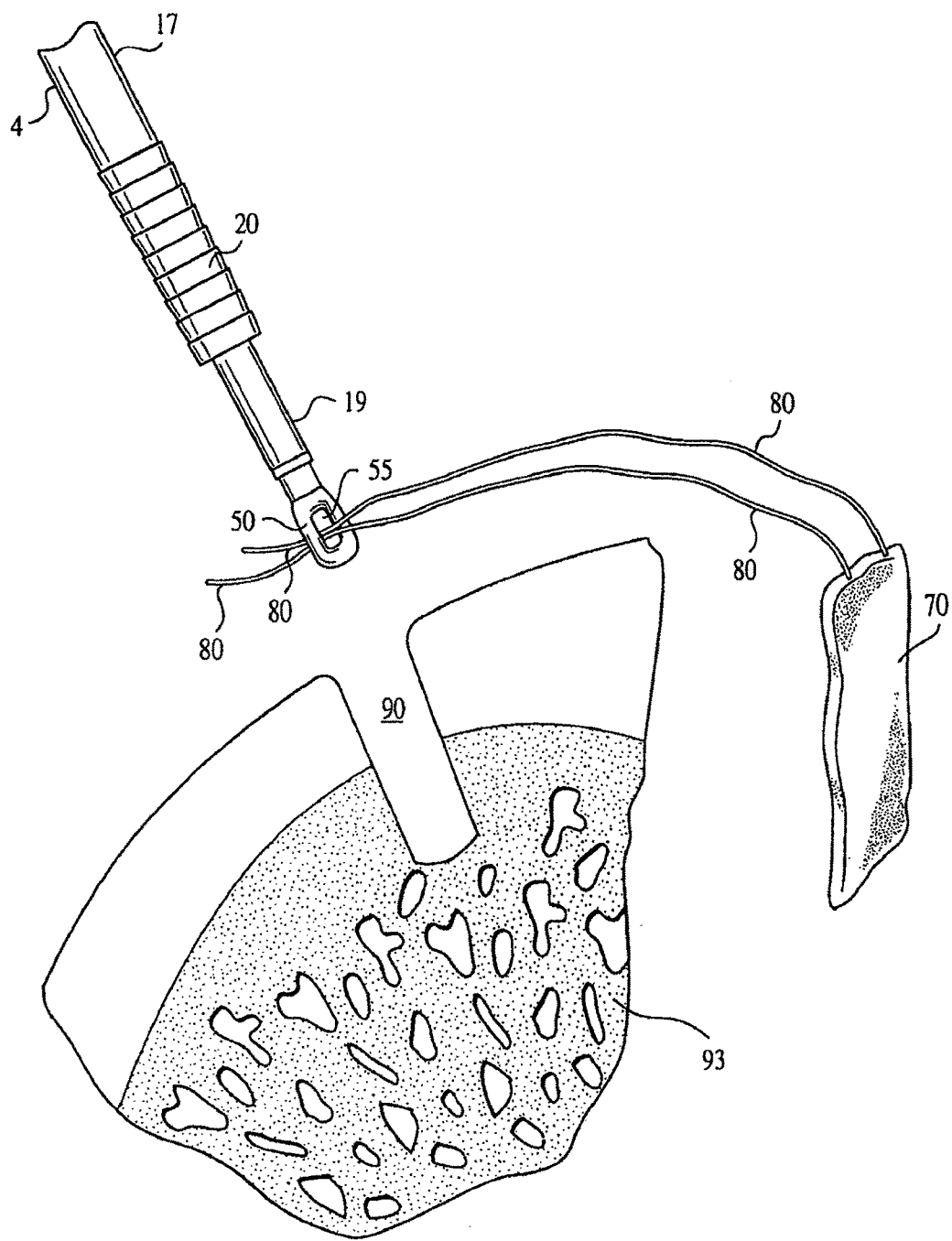
FIG. 4 is a schematic view of the surgical site of FIG. 3 undergoing a graft fixation technique with the push lock driver of FIGS. 1-2.

Next, as shown in FIG. 4, driver 100 with a pre-loaded interference device 20 and with the outer shaft 17 in the retracted position is provided in the proximity of the bone socket 90. Sutures 80 attached to the graft 70 are subsequently passed through the aperture 55 of the eyelet implant 50 at the end of driver 100, as shown in FIG. 4.

Figure 5:
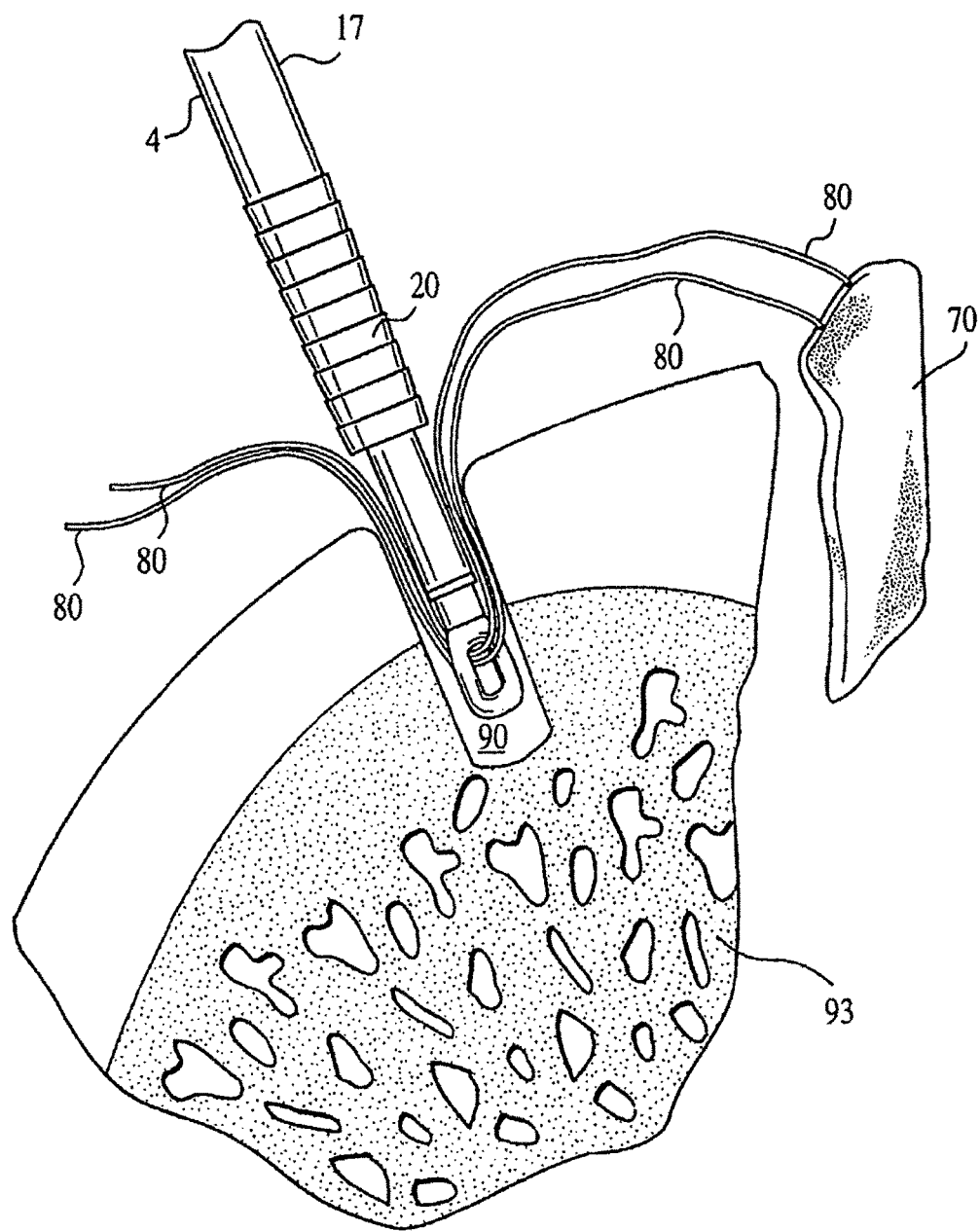
FIG. 5 is a schematic view of the surgical site of FIG. 3 undergoing a graft fixation technique with the push lock driver of FIGS. 1-2 and at a stage subsequent to that shown in FIG. 4.
Figure 6:
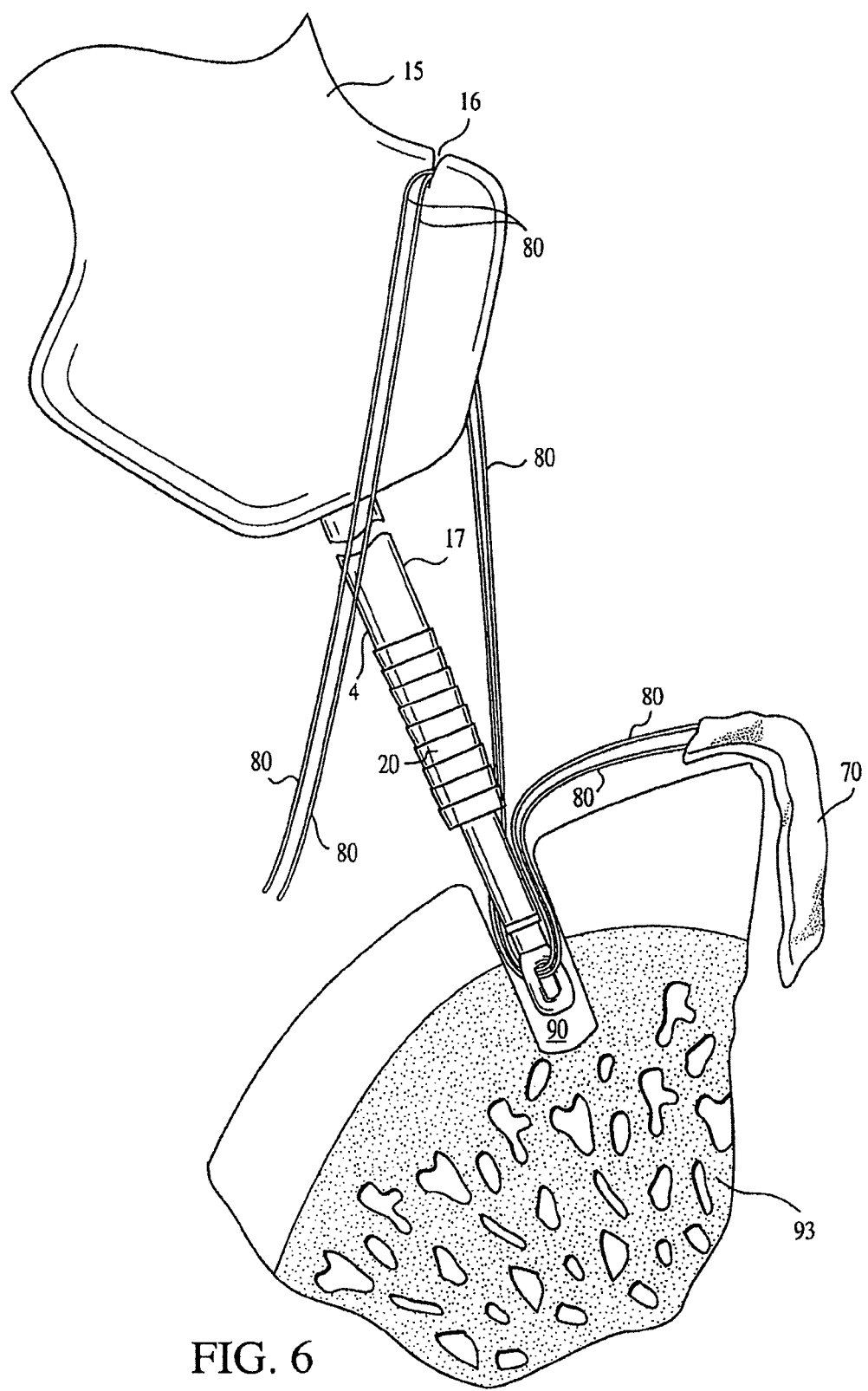
FIG. 6 is a schematic view of the surgical site of FIG. 3 undergoing a graft fixation technique with the push lock driver of FIGS. 1-2 and at a stage subsequent to that shown in FIG. 5.
Figure 7:
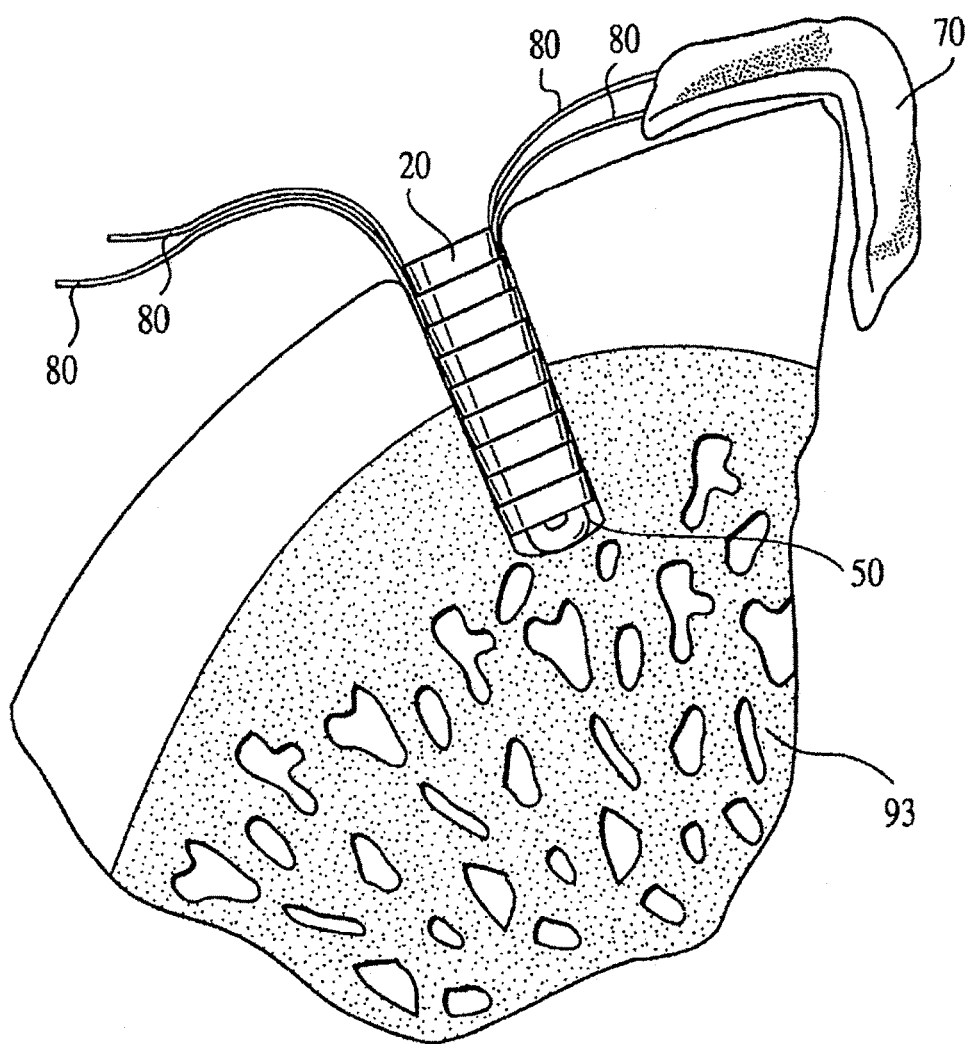
FIG. 7 is a schematic view of the surgical site of FIG. 3 undergoing a graft fixation technique with the push lock driver of FIGS. 1-2 and at a stage subsequent to that shown in FIG. 6.
Figure 8:
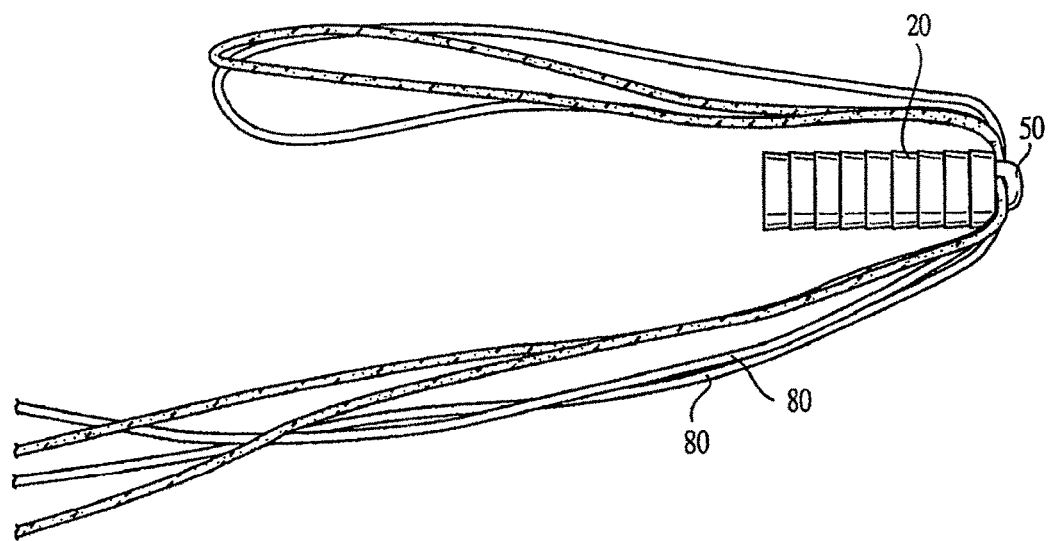
FIG. 8 is a schematic view of an eyelet implant of the present invention secured by and locked into an interference device, and in accordance with an embodiment of the present invention.

Referring now to FIG. 5, driver 100 is held with gentle pressure so that the eyelet implant 50 at the distal end 12 is held at the bottom of the hole 90, keeping the interference device 20 just outside the pilot hole 90. Tension is then applied to the suture 80 by wrapping the suture 80 around the slots 16 of the handle 15 and tensioning it, as shown in FIGS. 6-7. The suture 80 freely slides through aperture 55 of the eyelet implant 50, allowing the graft 70 to be positioned close to the edge of the pilot hole 90. Once tensioning of the suture 80 has been completed, the interference device 20 is then impacted into the pilot hole 90 so that the interference device 20 advances toward the distal end 12 of driver 100 and securely engages and locks in the eyelet implant 50 with the sutures 80, as shown in FIGS. 7-8. After the interference device 20 is fully inserted, the driver is removed and the ends of the sutures can be removed by clipping them short, leaving the graft 70 securely fastened to bone 93.

A significant advantage of the present invention is that the sutures attached to the graft or the graft itself can be securely attached to the bone without the need to tie knots. Additionally, the suture attached to the graft is secured both by the eyelet implant and by the interference device, along the bottom and sidewalls of the pilot hole between the bone and the screw or plug, conferring a much stronger fixation of the graft to the bone than is achievable with prior art procedures and devices. More importantly, the suture attached to the graft is allowed to freely slide though the aperture of the eyelet implant to allow precise advancement and guiding of the plug or screw into the blind hole or socket.

Figure 9:
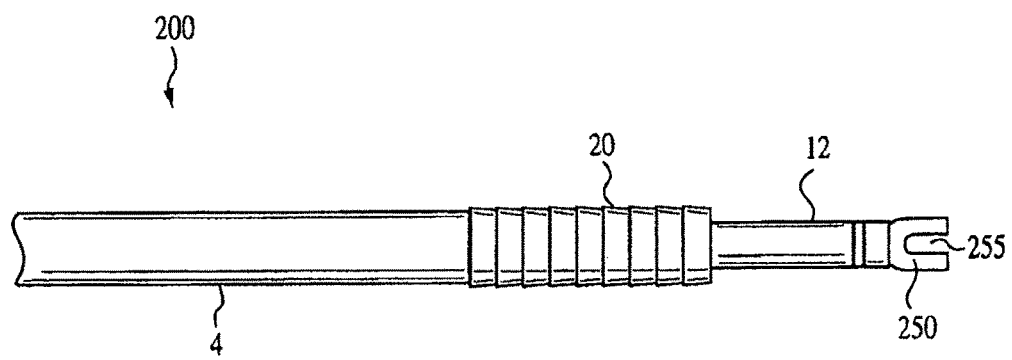
FIG. 9 illustrates a perspective view of a distal end of a push lock driver in accordance with a second embodiment of the present invention.

In another embodiment of the present invention illustrated in FIG. 9, driver 200 is provided with a horseshoe-shaped implant 250 (i.e., an implant with an open distal end) at the distal end of the driver in lieu of the eyelet implant. The horseshoe-shaped implant 250 is provided in the form of a wedge 255 that allows the suture attached to a graft to be securely contained within the wedge, yet be capable to freely slide within the wedge. The horseshoe-shaped implant 250 is formed of a transparent polymer material, and is preferably made of a bioabsorbable material such as PLLA, polyglycolic or polylactic acid polymers. Advantageously, the horseshoe-shaped implant 250 is made of a material similar to that of the interference device 20.

The horseshoe-shaped implant 250 may be detachable from the distal end 12 of the driver 200, similar to the eyelet implant described in detail above. In this embodiment, the detachable horseshoe-shaped implant 250 is securely engaged within the cannulated ribbed body of the interference plug or screw 20. Alternatively, the horseshoe-shaped implant 250 may be integral with the distal end 12 of the driver 200 and, after the interference screw or plug 20 is fully inserted into the pilot hole, the horseshoe-shaped implant 250 is removed from the site together with the driver 200.

Figure 10:
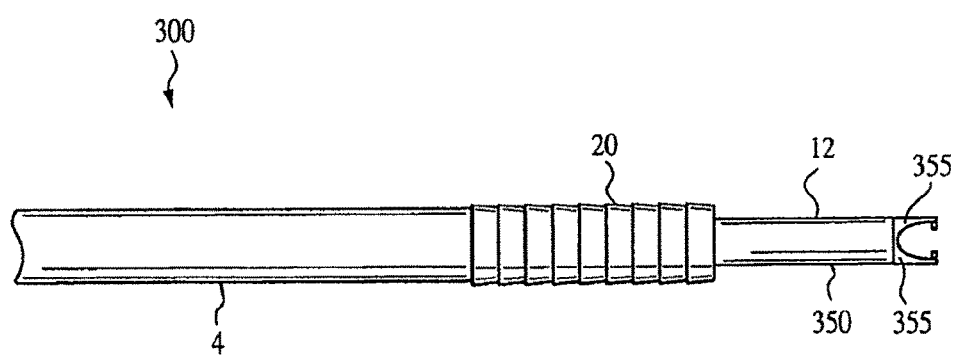
FIG. 10 illustrates a perspective view of a distal end of a push lock driver in accordance with a third embodiment of the present invention.

In yet another embodiment of the present invention and as illustrated in FIG. 10, driver 300 of the present invention is provided with a metal tubing 350 at the distal end of a driver, which in turn, is provided with a cut or pair of protuberances 355 at its most distal end to allow at least one end of a suture attached to a graft to be securely contained within the cut, yet be capable to freely slide within the cut. Preferably, the metal tubing 350 is integral with the distal end 12 of the driver 300 and, subsequent to the full insertion of the interference screw or plug 20 into the pilot hole, the metal tubing 350 is removed from the site together with the driver 300.

FIGS. 11-15 illustrate another embodiment of the present invention, according to which driver 400 is provided with a pointed tip implant 450 at the distal end of the driver, which is also an eyelet implant but which, because of its pointed tip, does not require the pre-drilling or pre-formation of a hole for fixating the device (implant with suture attached to graft) in the bone. The conical configuration of the most distal end of the pointed tip implant 450 allows the driver 400 with the attached implant to undergo a self-punching operation during graft fixation, eliminating any need to pre-drill a hole in the bone and providing increased fixation of the overall operation of securing the soft tissue. The conical configuration of the most distal end of the pointed tip implant 450 also provides suture fixation strength, as well as accelerated graft/tendon healing to bone. The pointed tip implant 450 may be detachable from the driver.

Figure 11:
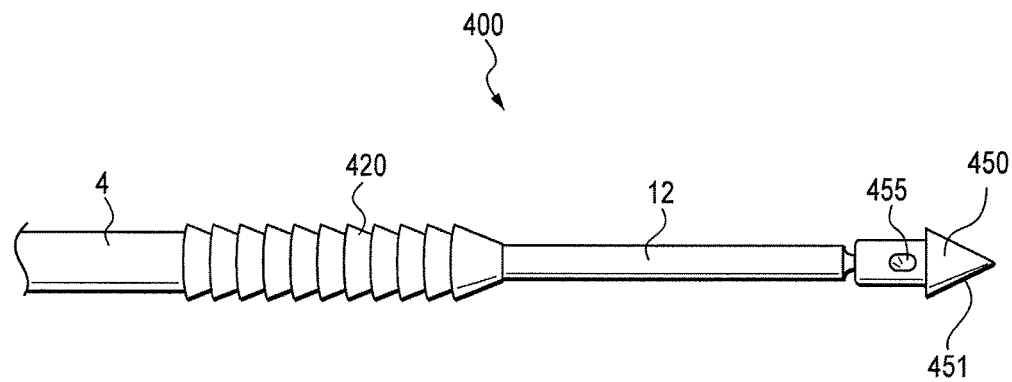
FIG. 11 illustrates a perspective view of a distal end of a push lock driver in accordance with a fourth embodiment of the present invention.
Figure 12:
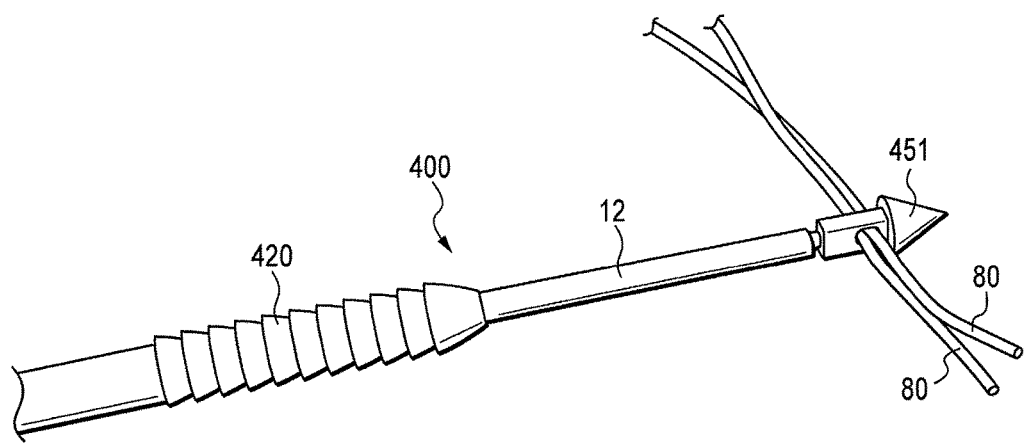
FIG. 12 illustrates another perspective view of the push lock driver of FIG. 11 with a strand passed through an aperture of the push lock.

As illustrated in FIGS. 11 and 12, pointed tip implant 450 is provided with an eyelet or aperture 455 for receiving at least one strand (for example, a suture strand) attached to a graft to pass through the eyelet implant 450. Pointed tip implant 450 is also provided, at its most distal end, with a conical portion 451 which allows direct advancement of the implant (by simply tapping the device with a mallet, for example) without the formation of a bone hole. Preferably, the conical portion 451 of the implant is formed of titanium or titanium alloy. In a preferred embodiment, eyelet or aperture 455 is also formed of titanium or similar material, to withstand impaction forces during the graft fixation procedure.

As in the previously-described first embodiment, strand 80 (attached to graft 70) is passed through the aperture 455 of the implant 450 at the end of the driver 400, as shown in FIGS. 11 and 12. Although FIG. 12 illustrate two strands 80 (i.e., two suture strands 80) passed through the aperture 455, the invention is not limited to this exemplary embodiment and contemplates additional embodiments wherein one strand or any number of strands are passed through the aperture 455. Preferably, at least one of the strands is formed of a high strength suture material such as FiberWire® suture, sold by Arthrex, Inc. of Naples, Fla., and described in U.S. Pat. No. 6,716,234, the disclosure of which is incorporated by reference herein. The high strength suture may be available in various lengths and widths. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE. The suture may optionally include filaments of various colors.

Figure 14:
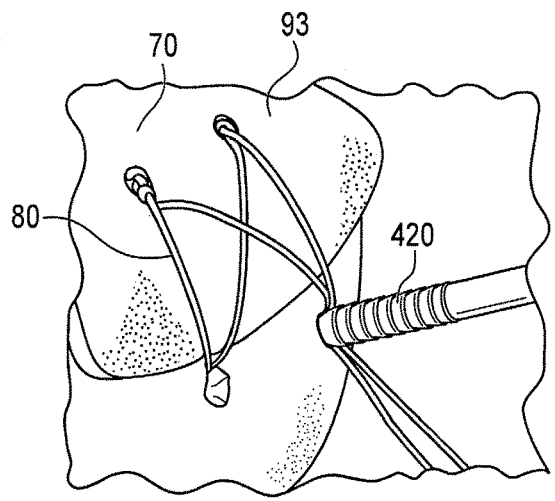
FIGS. 14 and 14A are schematic views of the surgical site of FIG. 13 at a graft fixation stage subsequent to that shown in FIG. 13.
Figure 15:
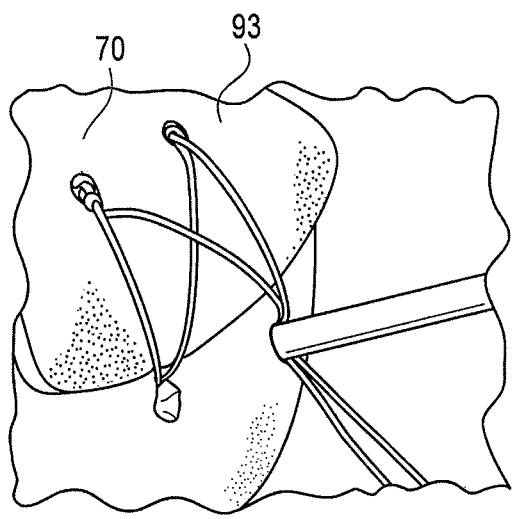
FIGS. 15 and 15A are schematic views of the surgical site of FIG. 13 at a graft fixation stage subsequent to that shown in FIGS. 14 and 14A.

An exemplary method of graft fixation using the pointed tip implant 450 of the present invention is illustrated with reference to FIGS. 13-15. This exemplary method illustrated in FIGS. 13-15 relates to a specific graft fixation technique (i.e., SutureBridge Lateral Row fixation); however, the invention is not limited to this exemplary embodiment and applies to any other method of soft tissue fixation known in the art.

Figure 13:
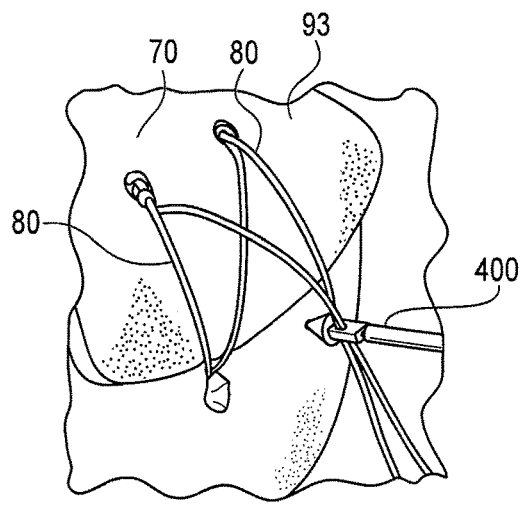
FIG. 13 is a schematic cross-sectional view of a surgical site undergoing a graft fixation technique with the push lock driver of FIGS. 11 and 12.
Figure 14A:
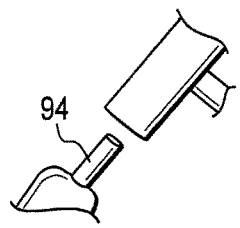
Figure 15A:
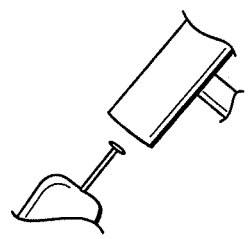

Referring to FIG. 13, an Arthrex SutureBridge ® medial row is completed as known in the art and the strands 80 (suture strands 80) are threaded through the titanium eyelet 455. As shown in FIGS. 14A, a protective cap 94 (or other device that prevents anchor deployment) is malleted to advance the PUSHLOCK® until the anchor contacts bone 93. The suture is then tensioned, as shown in FIG. 14. The protective cap 94 is subsequently removed (FIG. 15A) and the button 420 is malleted until mark (for example, a predefined laser line) is flush with the bone (FIG. 15). The ribbed, spiked configuration of plug or button 420 facilitates the insertion of the device 400 into the bone by simply exerting force upon the device, without the need to drill or form a hole in the bone.

Although the above embodiments have been described with reference to an implant, such as eyelet implant 50, 450 (FIGS. 1 and 11) or horseshoe-shaped implant 250 (FIG. 9), for example, having an aperture of a predefined configuration (i.e., eyelet or horseshoe configuration), it should be understood that the invention is not limited to these embodiments. Accordingly, the present invention also contemplates implants affixed to or detachable from a preloaded driver and having an aperture of any configuration or geometrical shape, as long as it captures suture and allows the captured suture to freely slide within the aperture.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A system for interference fixation of a suture in bone, comprising:
   a driver including a shaft having a proximal end and a distal end;
   an interference device situated on the shaft, the interference device having a length and an outer surface configured to engage bone; and
   an implant releasably attached near the distal end of the shaft with a spacing between the implant and the interference device, the spacing corresponding to the length of the interference device, a portion of the shaft being co-extensive with the spacing and exposed along the spacing, the implant having a suture-accommodating aperture for receiving a suture, the suture-accommodating aperture being aligned generally perpendicular to an axis between the proximal end and the distal end, the implant having a conical portion terminating in a pointed tip at its most distal end configured to establish a hole in bone for receiving the interference device;

wherein the driver includes a handle near the proximal end of the shaft, a portion of the handle being configured to be malleted to advance the implant in an insertion direction into bone without predrilling a hole in the bone and wherein the handle is manipulatable to advance the interference device in the insertion direction toward the implant into a suture securing position where the interference device secures the suture in the bone.

2. The system of claim 1, wherein the interference device is a screw.

3. The system of claim 1, wherein the interference device is a plug.

4. The system of claim 1, wherein the aperture of the implant has an eyelet configuration.

5. The system of claim 1, wherein
the shaft comprises an inner shaft at least partially received within an outer shaft; and
the implant is releasably attached to the inner shaft by a connector portion of the implant that fits within the distal end of the inner shaft.

6. The system of claim 1, wherein
the shaft includes an outer shaft disposed around an inner shaft and movable between a proximal position and a distal position along the inner shaft;
the interference device is loaded onto the inner shaft by inserting the inner shaft through a cannula of the interference device with the outer shaft retracted to the proximal position so that the proximal end of the loaded interference device abuts the distal end of the outer shaft; and
the handle is manipulatable to cause the outer shaft to advance from the proximal position to the distal position to advance the interference device toward the implant.

7. The system of claim 1, wherein the driver is useable in a first mode for urging the implant into bone and in a second mode for urging the interference device into bone.

8. The system of claim 1, wherein the interference device wedges suture between the interference device and bone.

9. The system of claim 1, wherein the interference device wedges suture in place to secure the suture without tying any knots.

10. The system of claim 1, wherein
the conical portion of the implant has a proximal end;
the proximal end of the conical portion defines a largest outside diameter of the implant; and
the spacing is determined between the proximal end of the conical portion and the interference device.

11. A surgical device, comprising:
a driver including a shaft having a proximal end and a distal end, the driver including a handle near the proximal end of the shaft;
a suture anchor situated at least partially on the driver, the suture anchor having a length; and
an implant releasably attached near the distal end of the shaft with a spacing between the implant and the suture anchor, the spacing corresponding to the length of the suture anchor, a portion of the shaft being co-extensive with the spacing and exposed along the spacing, the implant having a suture-accommodating aperture for receiving a suture, the suture-accommodating aperture being transverse to an insertion direction, the implant having a conical portion terminating in a pointed tip at its most distal end configured to establish a hole in bone for receiving the suture anchor;

wherein a portion of the handle is configured to be malleted to advance the implant in the insertion direction into bone without predrilling a hole in the bone and the handle is manipulatable to advance the suture anchor in the insertion direction toward the implant into a suture securing position where the suture anchor secures the suture in the bone.

12. The surgical device of claim 11, wherein
the suture anchor wedges suture in place relative to bone resulting from the driver causing the suture anchor to move away from the proximal end toward the aperture of the implant.

13. The surgical device of claim 11, wherein the suture anchor wedges suture between the suture anchor and bone.

14. The surgical device of claim 11, wherein the suture anchor comprises a screw.

15. The surgical device of claim 11, wherein the suture anchor comprises a plug.

16. The surgical device of claim 11, wherein the aperture of the implant has an eyelet configuration.

17. The surgical device of claim 11, wherein
the shaft comprises an inner shaft at least partially received within an outer shaft; and
the implant is releasably attached to the inner shaft by a connector portion of the implant that fits within a tubing near the distal end of the inner shaft.

18. The surgical device of claim 11, wherein the shaft includes an outer shaft disposed around an inner shaft and movable between a proximal position and a distal position along the inner shaft, and wherein the suture anchor is loaded onto the inner shaft by inserting the inner shaft through a cannula of the suture anchor with the outer shaft retracted to the proximal position so that the proximal end of the loaded suture anchor abuts a distal end of the outer shaft.

19. The surgical device of claim 11, wherein the driver is useable in a first mode for urging the implant into bone and in a second mode for urging the suture anchor into bone.

20. The surgical device of claim 11, wherein
the generally conical portion of the implant has a proximal end;
the proximal end of the conical portion defines a largest outside diameter of the implant; and
the spacing is determined between the proximal end of the generally conical portion and the suture anchor.

\* \* \* \* \*